US010172933B2

(12) United States Patent
Rieder et al.

(10) Patent No.: US 10,172,933 B2
(45) Date of Patent: Jan. 8, 2019

(54) MOSAIC VACCINES FOR SEROTYPE A FOOT-AND-MOUTH DISEASE VIRUS

(71) Applicants: The United States of America, as represented by the Secretary of Agriculture, Washington, DC (US); LOS ALAMOS NATIONAL SECURITY, LLC, Los Alamos, NM (US)

(72) Inventors: Aida E. Rieder, Westbrook, CT (US); William M. Fischer, Santa Fe, NM (US); Devendra K. Rai, Old Saybrook, CT (US)

(73) Assignee: The United States of America, as represented by The Secretary of Agriculture, Washington, DC (US)

(*) Notice: Subject to any disclaimer, the term of this patent is extended or adjusted under 35 U.S.C. 154(b) by 0 days.

(21) Appl. No.: 15/785,875

(22) Filed: Oct. 17, 2017

(65) Prior Publication Data
US 2018/0117138 A1 May 3, 2018

Related U.S. Application Data

(60) Provisional application No. 62/415,124, filed on Oct. 31, 2016.

(51) Int. Cl.
A61K 39/135 (2006.01)
C12N 7/00 (2006.01)
A61K 39/12 (2006.01)
A61K 39/00 (2006.01)

(52) U.S. Cl.
CPC ............ A61K 39/135 (2013.01); A61K 39/12 (2013.01); C12N 7/00 (2013.01); A61K 2039/55566 (2013.01); C12N 2770/32122 (2013.01); C12N 2770/32134 (2013.01)

(58) Field of Classification Search
None
See application file for complete search history.

(56) References Cited

U.S. PATENT DOCUMENTS 9,145,548 B2 9/2015 Fowler et al.
2015/0306203 A1 10/2015 Wang et al.
2016/0220659 A1 8/2016 Audonnet et al.

OTHER PUBLICATIONS

GenBank: AHW42489.1. P1, partial [Foot-and-mouth disease virus—type A]. Dated Mar. 4, 2015.*
GenBank: AGO58323.1. capsid protein, partial [Foot-and-mouth disease virus—type A]. Dated Feb. 25, 2014.*
Xiao, Yan et al., Large-scale production of foot-and-mouth disease virus (serotype Asia1) VLP vaccine in *Escherichia coli* and protection potency evaluation in cattle, BMC Biotechnology, (2016), 16(56):1-9.
GenBank: AHW42489.1, P1, partial [Foot-and-mouth disease virus—type A], Mar. 4, 2015.
GenBank: AG058323.1, capsid protein, partial [Foot-and-mouth disease virus—type A], Feb. 25, 2014.
International Searching Authority, PCT/US2017/058295 for the United States of America, as Represented by the Secretary of Agriculture, International Filing Date Oct. 10, 2017.

* cited by examiner

Primary Examiner — Nianxiang Zou
(74) Attorney, Agent, or Firm — John D. Fado; Mark D. McNemar

(57) ABSTRACT

Synthetic foot-and-mouth disease virus (FMDV) mosaic polypeptides, and nucleic acid molecules encoding the mosaic polypeptides, are described. The mosaic polypeptides have greater T-cell epitope coverage than naturally occurring FMDV polypeptides, and include common FMDV epitopes, but exclude rare FMDV epitopes. When included as part of an FMDV genome, the mosaic polypeptides permit virus replication and assembly into FMDV particles. The mosaic polypeptide and nucleic acid compositions can be used to elicit immune responses that provide protection against a broad range of serotype A FMDV strains.

18 Claims, 6 Drawing Sheets
(5 of 6 Drawing Sheet(s) Filed in Color)
Specification includes a Sequence Listing.

|  | BHK-21 22 hours | Titer PFU/ml |
|---|---|---|
| vA24Cru WT | | $2.6 \times 10^7$ |
| vA24$^{Mosaic}$ 2.2 | | $3.1 \times 10^7$ |
| vA24$^{Mosaic}$ 2.1 | | $1.65 \times 10^7$ |

FIG. 3

ID NO: 2) or mosaic polypeptide

SEQUENCE LISTING

<160> NUMBER OF SEQ ID NOS: 8

<210> SEQ ID NO 1
<211> LENGTH: 2205
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 1

```
ggggccggcc aatccagtcc ggcgaccggc tcgcagaacc aatctggcaa cactggcagc      60
ataattaaca actactacat gcagcaatac cagaactcca tggacacaca gttgggagac     120
aatgccatca gtggaggctc caacgagggc tccacggaca caacttcaac acacacaacc     180
aacactcaaa acaatgactg gttctcgaag ctcgccagtt cagcttttac cggtctgttc     240
ggtgcactgc tcgccgacaa gaagacgag gaaacgacac ttcttgagga ccgcatcctc     300
accacccgca acgggcacac cacctcgacg acccaatcga gtgtgggtgt cacatacggg     360
tactccacag gggaggacca cgtttctggg cccaacacat cgggcctgga gacgcgagtg     420
gtgcaggcag agagattctt caaaaagttc ttgtttgact ggacaacgga caagccattt     480
ggacacctgg aaaagctgga gctcccgacc gaccacaagg gtgtctacgg acacttggtg     540
gactcgttcg cctatatgag aaatggctgg gatgttgagg tgtccgctgt tggcaaccag     600
ttcaacggcg ggtgcctcct ggtggccatg gtacctgaat ggaagaaatt tacaacacgg     660
gagaaatacc aactcaccct ttttcccgcac cagtttatta accccagaac taacatgact     720
gcccacatcg tggtcccta ccttggtgtg aacaggtatg atcagtacaa gaagcataag     780
ccctggacat tggttgtcat ggtcgtgtcg ccacttacga ccacaagcat tggtgcgaca     840
caaatcaagg tctacgccaa catagctccg acctatgttc acgtggccgg tgaactcccc     900
tcgaaagagg ggattgtccc ggttgcatgt gcggacggtt acggaggatt ggtgacgaca     960
gacccgaaga cagctgaccc tgtttatggc atggtgtaca acccgcctag gactaacttc    1020
cctgggcgct tcaccaacct gttggacgtg gccgaagcgt gtcccacttt cctctgcttt    1080
gacaacggga aaccgtacgt cgtcacgcgg acggatgaac agcgactttt ggccaagttt    1140 gaccttccc ttgccgcaaa acatatgtcc aacacatacc tgtcagggat tgctcagtac    1200
tacgcacagt actctggcac catcaatttg catttcatgt tcacaggttc cactgattca    1260
aaggcccgat acatggtggc ctacgtccca cctgggtgg agacaccacc ggacacacct    1320
gaaagggctg cccactgcat tcacgctgaa tgggacactg gactaaactc caaattcact    1380
ttctcaatcc cgtacatgtc cgccgcggat tacgcgtaca cagcgtctga cacggcagaa    1440
acaaccaacg tacagggatg ggtctgcgtc taccaaatta cacacgggaa ggctgaaaat    1500
gacaccttgg tcgtgtcggc cagcgccggc aaagactttg agttgcgcct cccgattgac    1560
ccccgcgcgc agaccaccgc taccgggaa tcagcagacc cggtcaccac cgccgtggag    1620
aactacggcg gtgagacaca agtccagaga cgtcaccaca cggacgttag tttcatcatg    1680
```

```
gacagatttg tgaagatcgg aaccactaac ccaacacatg tcattgacct catgcagact   1740
caccaacacg gtctggtggg tgccttgctg cgtgcagcca cgtactactt ttctgacctg   1800
gaaattgttg tacggcacga aggcaatctg acctgggtgc ccaacggcgc ccctgaagca   1860
gccctgtcca acacaggaaa ccccactgcc tacaacaagg caccattcac gagactcgct   1920
ctcccctaca ctgcgccgca ccgtgtgctg gcaacagtgt acaacgggac gaacaagtac   1980
tccgcggcca gtgggcgcac aagaggcgac ttggggcaac tcgcggcgcg aatcgcggca   2040
cagcttcctg cttcatttaa cttcggtgca atcaaggccg acgccatcca cgaacttctc   2100
gtgcgcatga acgggccga gctctactgc cccagaccgc tgttggcaat agaggtgtct   2160
tcgcaagaca ggtacaagca aaagatcatt gcaccagcaa agcag              2205
```

<210> SEQ ID NO 2
<211> LENGTH: 735
<212> TYPE: PRT
<213> ORGANISM: ARTIFICIAL SEQUENCE
<220> FEATURE:
<223> OTHER INFORMATION: CHEMICALLY SYNTHESIZED

<400> SEQUENCE: 2

```
Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Ser Thr His Thr Thr Asn Thr Gln Asn
    50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Glu Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ser Thr Gly Glu Asp His Val
        115                 120                 125

Ser Gly Pro Asn Thr Ser Gly Leu Glu Thr Arg Val Val Gln Ala Glu
    130                 135                 140

Arg Phe Phe Lys Lys Phe Leu Phe Asp Trp Thr Thr Asp Lys Pro Phe
145                 150                 155                 160

Gly His Leu Glu Lys Leu Glu Leu Pro Thr Asp His Lys Gly Val Tyr
                165                 170                 175

Gly His Leu Val Asp Ser Phe Ala Tyr Met Arg Asn Gly Trp Asp Val
            180                 185                 190

Glu Val Ser Ala Val Gly Asn Gln Phe Asn Gly Gly Cys Leu Leu Val
        195                 200                 205

Ala Met Val Pro Glu Trp Lys Lys Phe Thr Thr Arg Glu Lys Tyr Gln
    210                 215                 220

Leu Thr Leu Phe Pro His Gln Phe Ile Asn Pro Arg Thr Asn Met Thr
225                 230                 235                 240

Ala His Ile Val Val Pro Tyr Leu Gly Val Asn Arg Tyr Asp Gln Tyr
                245                 250                 255

Lys Lys His Lys Pro Trp Thr Leu Val Val Met Val Val Ser Pro Leu
            260                 265                 270
```

```
Thr Thr Thr Ser Ile Gly Ala Thr Gln Ile Lys Val Tyr Ala Asn Ile
            275                 280                 285

Ala Pro Thr Tyr Val His Val Ala Gly Glu Leu Pro Ser Lys Glu Gly
    290                 295                 300

Ile Val Pro Val Ala Cys Ala Asp Gly Tyr Gly Gly Leu Val Thr Thr
305                 310                 315                 320

Asp Pro Lys Thr Ala Asp Pro Val Tyr Gly Met Val Tyr Asn Pro Pro
                325                 330                 335

Arg Thr Asn Phe Pro Gly Arg Phe Thr Asn Leu Leu Asp Val Ala Glu
            340                 345                 350

Ala Cys Pro Thr Phe Leu Cys Phe Asp Asn Gly Lys Pro Tyr Val Val
        355                 360                 365

Thr Arg Thr Asp Glu Gln Arg Leu Leu Ala Lys Phe Asp Leu Ser Leu
    370                 375                 380

Ala Ala Lys His Met Ser Asn Thr Tyr Leu Ser Gly Ile Ala Gln Tyr
385                 390                 395                 400

Tyr Ala Gln Tyr Ser Gly Thr Ile Asn Leu His Phe Met Phe Thr Gly
                405                 410                 415

Ser Thr Asp Ser Lys Ala Arg Tyr Met Val Ala Tyr Val Pro Pro Gly
            420                 425                 430

Val Glu Thr Pro Pro Asp Thr Pro Glu Arg Ala Ala His Cys Ile His
        435                 440                 445

Ala Glu Trp Asp Thr Gly Leu Asn Ser Lys Phe Thr Phe Ser Ile Pro
    450                 455                 460

Tyr Met Ser Ala Ala Asp Tyr Ala Tyr Thr Ala Ser Asp Thr Ala Glu
465                 470                 475                 480

Thr Thr Asn Val Gln Gly Trp Val Cys Val Tyr Gln Ile Thr His Gly
                485                 490                 495

Lys Ala Glu Asn Asp Thr Leu Val Val Ser Ala Ser Ala Gly Lys Asp
            500                 505                 510

Phe Glu Leu Arg Leu Pro Ile Asp Pro Arg Ala Gln Thr Thr Ala Thr
        515                 520                 525

Gly Glu Ser Ala Asp Pro Val Thr Thr Ala Val Glu Asn Tyr Gly Gly
    530                 535                 540

Glu Thr Gln Val Gln Arg Arg His His Thr Asp Val Ser Phe Ile Met
545                 550                 555                 560

Asp Arg Phe Val Lys Ile Gly Thr Thr Asn Pro Thr His Val Ile Asp
                565                 570                 575

Leu Met Gln Thr His Gln His Gly Leu Val Gly Ala Leu Leu Arg Ala
            580                 585                 590

Ala Thr Tyr Tyr Phe Ser Asp Leu Glu Ile Val Val Arg His Glu Gly
        595                 600                 605

Asn Leu Thr Trp Val Pro Asn Gly Ala Pro Glu Ala Ala Leu Ser Asn
    610                 615                 620

Thr Gly Asn Pro Thr Ala Tyr Asn Lys Ala Pro Phe Thr Arg Leu Ala
625                 630                 635                 640

Leu Pro Tyr Thr Ala Pro His Arg Val Leu Ala Thr Val Tyr Asn Gly
                645                 650                 655

Thr Asn Lys Tyr Ser Ala Ala Ser Gly Arg Thr Arg Gly Asp Leu Gly
            660                 665                 670

Gln Leu Ala Ala Arg Ile Ala Ala Gln Leu Pro Ala Ser Phe Asn Phe
        675                 680                 685

Gly Ala Ile Lys Ala Asp Ala Ile His Glu Leu Leu Val Arg Met Lys
```

```
                690              695              700
Arg Ala Glu Leu Tyr Cys Pro Arg Pro Leu Leu Ala Ile Glu Val Ser
705              710              715              720

Ser Gln Asp Arg Tyr Lys Gln Lys Ile Ile Ala Pro Ala Lys Gln
                725              730              735

<210> SEQ ID NO 3
<211> LENGTH: 2202
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 3
ggggccggcc aatccagtcc ggcgaccggc tcgcagaacc aatctggcaa cactggcagc      60
ataattaaca actactacat gcagcaatac cagaactcca tggacacaca gttgggagac     120
aatgccatca gtggaggctc aacgagggc tccacggaca caacttcaac acacacaacc     180
aacactcaaa acaatgactg gttctcgaag ctcgccagtt cagcttttac cggtctgttc     240
ggtgcactgc tcgccgacaa gaagacagag gaaatcacac ttcttgagga ccgcatcctc     300
accacccgca acgggcacac catctcgacg acccaatcga gtgtgggtgt cacatacggg     360
tactccacag aggaggacca cgttgctggg cccaacacat cgggcctgga gacgcgagtg     420
gtgcaggcag agagattctt caaaaagcac ttgtttgact ggacaacgga caaggcattt     480
ggacacctgg aaaagctgga gctcccgacc gaacacaagg gtgtctacgg acacttggtg     540
gactcgtacg cctatatgag aaatggctgg gatgttgagg tgaccgctgt tggcaaccag     600
ttcaacggcg ggtgcctcct ggtggccatg gtacctgaat ggaaggaatt tacccacgg      660
gagaaatacc aactcaccct tttcccgcac cagtttatta gccccagaac taacatgact     720
gcccacatca cggtccccta ccttggtgtg aacaggtatg atcagtacaa gcagcataag     780
ccctggacat tggttgtcat ggtcgtgtcg ccacttacga ccagcagcat ggtgcgtca      840
caaatcaagg tctacgccaa catagctccg acccatgttc acgtggccgg tgaactcccc     900
tcgaaagagg ggattgtccc ggttgcatgt tcggacggtt acgaggatt ggtgacgaca      960
gacccgaaga cagctgaccc tgcttatggc aaggtgtaca acccgcctag gactaactac    1020
cctgggcgct tcaccaacct gttggacgtg gccgaagcgt gtcccacttt cctctgcttt    1080
gacgacggga accgtacgt cgtcacgcgg acggatgacc agcgactttt ggccaagttt     1140
gacgtttccc ttgccgcaaa acatatgtcc aacacatacc tggcagggct tgctcagtac    1200
tacacacagt actctggcac catcaatttg catttcatgt tcacaggttc cactgagtca    1260
aaggcccgat acatggtggc ctacatccca cctggggtgg agacaccacc ggacacacct    1320
gaaaaggctg cccactgcat tcacgctgaa tgggacactg gactaaactc caaattcact    1380
ttctcaatcc cgtacgtatc cgccgcggat tacgcgtaca cagcgtctga cgtggcagaa    1440
acaaccaacg tacagggatg ggtctgcatc taccaaatta cacacgggaa ggctgaacaa    1500
gacaccttgg tcgtgtcggt tagcgccggc aaagactttg agttgcgcct cccgattgac    1560
ccccgcacgc agaccaccac tgccggggaa tcagcagacc cggtcaccac caccgtggag    1620
aactacggcg gtgagacaca agcccagaga cgtcaccaca cggacgttgg tttcatcatg    1680
gacagatttg tgaagatcgg aaacacgagc ccaacacatg tcattgacct catgcagact    1740
caccaacacg ctctggtggg tgccttgctg cgtcagccac gtactactt ttctgacctg      1800
gaaattgttg tacggcacga cggcaatctg acctgggtgc ccaacggcgc ccctgtagaa    1860
```

```
gctctggcga acaccagcaa ccccactgcc taccacaagc aaccattcac gagactcgct   1920 ctccctaca  ctgcgccgca ccgtgtgctg gcaacagtgt acaacgggac gagtaagtac   1980
tccgcgcctg ctacaagaag aggcgacttg gggtctctcg cggcgcgagt cgcggcacag   2040
cttccttctt catttaactt cggtgcaatc agggccacca ccatccacga acttctcgtg   2100
cgcatgagac gggccgagct ctactgcccc agaccgctgt tggcagtaga ggtgtcttcg   2160
caagacaggc acaagcaaaa gatcattgca ccagcaaggc ag                     2202
```

```
<210> SEQ ID NO 4
<211> LENGTH: 734
<212> TYPE: PRT
<213> ORGANISM: ARTIFICIAL SEQUENCE
<220> FEATURE:
<223> OTHER INFORMATION: CHEMICALLY SYNTHESIZED

<400> SEQUENCE: 4
```

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Glu Ile Thr Leu Leu Glu
                85                  90                  95

Asp Arg Ile Leu Thr Thr Arg Asn Gly His Thr Ile Ser Thr Thr Gln
            100                 105                 110

Ser Ser Val Gly Val Thr Tyr Gly Tyr Ser Thr Glu Glu Asp His Val
        115                 120                 125

Ala Gly Pro Asn Thr Ser Gly Leu Glu Thr Arg Val Val Gln Ala Glu
    130                 135                 140

Arg Phe Phe Lys Lys His Leu Phe Asp Trp Thr Thr Asp Lys Ala Phe
145                 150                 155                 160

Gly His Leu Glu Lys Leu Glu Leu Pro Thr Glu His Lys Gly Val Tyr
                165                 170                 175

Gly His Leu Val Asp Ser Tyr Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Met Val Pro Glu Trp Lys Glu Phe Thr Pro Arg Glu Lys Tyr Gln
    210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Gln His Lys Pro Trp Thr Leu Val Val Met Val Val Ser Pro Leu
            260                 265                 270

Thr Thr Ser Ser Ile Gly Ala Ser Gln Ile Lys Val Tyr Ala Asn Ile
        275                 280                 285

Ala Pro Thr His Val His Val Ala Gly Glu Leu Pro Ser Lys Glu Gly
    290                 295                 300

```
Ile Val Pro Val Ala Cys Ser Asp Gly Tyr Gly Gly Leu Val Thr Thr
305                 310                 315                 320

Asp Pro Lys Thr Ala Asp Pro Ala Tyr Gly Lys Val Tyr Asn Pro Pro
            325                 330                 335

Arg Thr Asn Tyr Pro Gly Arg Phe Thr Asn Leu Leu Asp Val Ala Glu
            340                 345                 350

Ala Cys Pro Thr Phe Leu Cys Phe Asp Asp Gly Lys Pro Tyr Val Val
            355                 360                 365

Thr Arg Thr Asp Asp Gln Arg Leu Leu Ala Lys Phe Asp Val Ser Leu
        370                 375                 380

Ala Ala Lys His Met Ser Asn Thr Tyr Leu Ala Gly Leu Ala Gln Tyr
385                 390                 395                 400

Tyr Thr Gln Tyr Ser Gly Thr Ile Asn Leu His Phe Met Phe Thr Gly
            405                 410                 415

Ser Thr Glu Ser Lys Ala Arg Tyr Met Val Ala Tyr Ile Pro Pro Gly
            420                 425                 430

Val Glu Thr Pro Pro Asp Thr Pro Glu Lys Ala Ala His Cys Ile His
        435                 440                 445

Ala Glu Trp Asp Thr Gly Leu Asn Ser Lys Phe Thr Phe Ser Ile Pro
450                 455                 460

Tyr Val Ser Ala Ala Asp Tyr Ala Tyr Thr Ala Ser Asp Val Ala Glu
465                 470                 475                 480

Thr Thr Asn Val Gln Gly Trp Val Cys Ile Tyr Gln Ile Thr His Gly
            485                 490                 495

Lys Ala Glu Gln Asp Thr Leu Val Val Ser Val Ser Ala Gly Lys Asp
            500                 505                 510

Phe Glu Leu Arg Leu Pro Ile Asp Pro Arg Thr Gln Thr Thr Thr Ala
        515                 520                 525

Gly Glu Ser Ala Asp Pro Val Thr Thr Val Glu Asn Tyr Gly Gly
        530                 535                 540

Glu Thr Gln Ala Gln Arg Arg His His Thr Asp Val Gly Phe Ile Met
545                 550                 555                 560

Asp Arg Phe Val Lys Ile Gly Asn Thr Ser Pro Thr His Val Ile Asp
                565                 570                 575

Leu Met Gln Thr His Gln His Ala Leu Val Gly Ala Leu Leu Arg Ala
            580                 585                 590

Ala Thr Tyr Tyr Phe Ser Asp Leu Glu Ile Val Val Arg His Asp Gly
        595                 600                 605

Asn Leu Thr Trp Val Pro Asn Gly Ala Pro Val Glu Ala Leu Ala Asn
        610                 615                 620

Thr Ser Asn Pro Thr Ala Tyr His Lys Gln Pro Phe Thr Arg Leu Ala
625                 630                 635                 640

Leu Pro Tyr Thr Ala Pro His Arg Val Leu Ala Thr Val Tyr Asn Gly
            645                 650                 655

Thr Ser Lys Tyr Ser Ala Pro Ala Thr Arg Arg Gly Asp Leu Gly Ser
            660                 665                 670

Leu Ala Ala Arg Val Ala Ala Gln Leu Pro Ser Ser Phe Asn Phe Gly
        675                 680                 685

Ala Ile Arg Ala Thr Thr Ile His Glu Leu Leu Val Arg Met Arg Arg
        690                 695                 700

Ala Glu Leu Tyr Cys Pro Arg Pro Leu Leu Ala Val Glu Val Ser Ser
705                 710                 715                 720
```

Gln Asp Arg His Lys Gln Lys Ile Ile Ala Pro Ala Arg Gln
                    725                 730

```
<210> SEQ ID NO 5
<211> LENGTH: 26
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 5
agcggagcat gacggccgtg ggaccc                                         26

<210> SEQ ID NO 6
<211> LENGTH: 21
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 6
tgttcggtgc actgctcgcc g                                              21

<210> SEQ ID NO 7
<211> LENGTH: 21
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 7
tgttcggtgc actgctcgcc g                                              21

<210> SEQ ID NO 8
<211> LENGTH: 36
<212> TYPE: DNA
<213> ORGANISM: ARTIFICIAL SEQUENCE
<220> FEATURE:
<223> OTHER INFORMATION: CHEMICALLY SYNTHESIZED

<400> SEQUENCE: 8
tcaacgtctc cggctagctt aagcaggtca aaattc                              36
```

MOSAIC VACCINES FOR SEROTYPE A FOOT-AND-MOUTH DISEASE VIRUS

CROSS-REFERENCE

This application claims priority under 35 U.S.C. § 119(e) to U.S. Provisional Ser. No. 62/415,124 filed Oct. 31, 2016, the contents of which are hereby incorporated by reference herein in their entirety.

ACKNOWLEDGMENT OF GOVERNMENT SUPPORT

This invention was made with government support under Contract No. DE-AC52-06NA25396, awarded by the U.S. Department of Energy. The government has certain rights in the invention.

FIELD OF INVENTION

This disclosure concerns synthetic foot-and-mouth disease virus (FMDV) polypeptides and nucleic acids and their use for inducing a broad immune response against serotype A FMDV.

BACKGROUND OF THE INVENTION

FMDV causes a livestock disease with significant economic impact in endemic regions where it currently circulates. Furthermore, FMDV has the potential for great economic damage were it to be introduced into FMDV-free areas. Current "kill, burn, and bury" outbreak control strategies are unsatisfactory for economic, humane, and strategic reasons (Breeze, *Biosecur Bioterro* 2(4): 254-264, 2004). Although vaccination could be an integral part of outbreak management, available vaccines, which are based on inactivated virus, are unsatisfactory in terms of cost, production safety, duration of immunity, and breadth of protection (Rodriguez and Gay, *Expert Rev Vaccines* 10(3):377-387, 2011; Robinson et al., *Transbound Emerg Dis* 63 (Suppl 1):30-41, 2016. Outside of North America, the European Union, Australia and New Zealand, FMDV circulates widely. FMDV is durable in the environment and highly infectious. The direct economic impact of an FMDV outbreak in the U.S. is estimated at tens of billions to hundreds of billions of dollars, with rapid and extensive vaccination possibly reducing the cost by one-half (Schroeder et al., *Journal of Agricultural and Applied Economics* 47:47-76, 2015).

FMDV has seven major serotypes, four that are widespread (A, O, C, and Asia-1), and three predominantly found in sub-Saharan Africa (SAT-1, SAT-2, and SAT-3). Within-serotype diversity is high, and there is little cross-protection even between isolates of the same serotype. In view of this diversity, each outbreak needs to be field-matched to one of many vaccine strains. Recent developments in FMDV vaccines have led to improvements in many areas (Robinson et al., *Transbound Emerg Dis* 63 (Suppl 1):30-41, 2016), but breadth of protection is still limited; most vaccines only protect against outbreaks closely related to the vaccine strain, so protection against all possible outbreaks would require prohibitively large stockpiles.

Thus, a need remains to improve the breadth of vaccine-induced protection from different strains of FMDV.

SUMMARY OF THE INVENTION

Disclosed herein are FMDV mosaic polypeptides that provide higher levels of T-cell epitope coverage compared to natural FMDV polypeptides, with minimal unnatural and rare epitopes. The mosaic polypeptide and nucleic acid compositions disclosed herein can be used to elicit immune responses that provide protection against a broad range of serotype A FMDV strains.

Provided herein are synthetic FMDV polypeptides having an amino acid sequence at least 98% identical to mosaic polypeptide VP4.2.1 (SEQ ID NO: 2) or mosaic polypeptide VP4.2.2 (SEQ ID NO: 4). Recombinant FMDV that include the mosaic polypeptides are also provided.

Further provided are nucleic acid molecules and vectors encoding the mosaic VP4.2.1 and VP4.2.2 polypeptides. In some embodiments, the vectors include coding sequences for the remaining FMDV proteins such that upon transfection of the vector into a permissive host cell, infectious FMDV is produced.

Compositions that include one or both of the mosaic FMDV polypeptides, or nucleic acid molecules encoding one or both of the mosaic FMDV polypeptides, are also provided by the present disclosure. In some examples, the composition includes a recombinant FMDV that includes the mosaic polypeptide, or two recombinant FMDV, each with a different mosaic FMDV polypeptide.

Also provided herein are methods of eliciting an immune response against FMDV in subject, and methods of immunizing a subject against FMDV, by administering to the subject a mosaic FMDV polypeptide, nucleic acid molecule, vector, recombinant FMDV or composition disclosed herein.

The foregoing and other objects, features, and advantages of the invention will become more apparent from the following detailed description, which proceeds with reference to the accompanying figures.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

FIGS. 2A-2C show the coverage of potential FMDV capsid epitopes by different vaccine candidates. (FIG. 2A) Coverage of 1-, 2-, and 3-mosaic cocktails compared with natural sequence cocktails of the same size. (FIG. 2B) Phylogenetic distribution of capsid proteins of FMDV serotype A, as covered by the natural strain A24 Cruzeiro (left), or by the 2-sequence mosaic cocktail disclosed herein (right). (FIG. 2C) Coverage of viral variants by year of isolation. Mosaics cover recent isolates much better than the natural-strain A24 vaccine. Blue lines indicate decadal means.

FIG. 3 shows tissue-culture propagation and plaque morphology of infectious-nucleic-acid mosaic constructs. Viral plaques (centers of viral replication) are seen as light spots on the darker background of uninfected cells in the plate.

SEQUENCES

Figure 1:
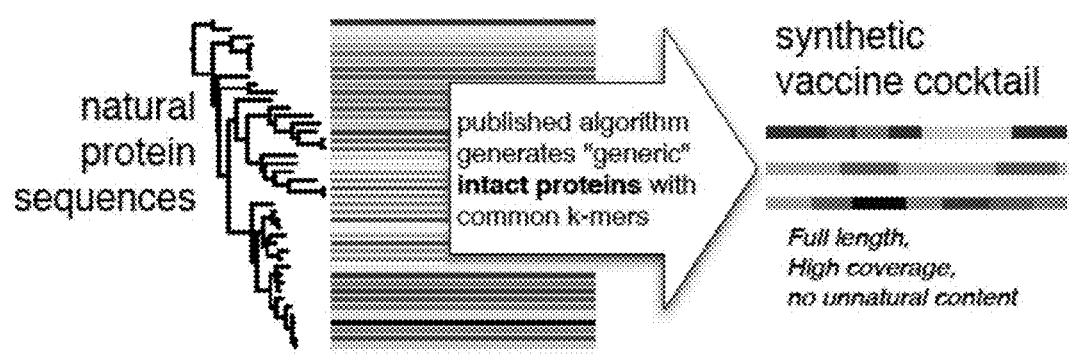
FIG. 1 is a schematic of the mosaic immunogen design method. The figure shows a conceptual illustration of the method whereby a selection of natural protein sequences is selected (by inspection) and processed by the mosaic algorithm described in Fischer et al. (*Nat Med* 13:100-106, 2007) to generate synthetic high-coverage sequences.

SEQ ID NO: 1 is the nucleotide sequence of the mosaic FMDV-VP4.2.1 capsid:

```
GGGGCCGGCCAATCCAGTCCGGCGACCGGCTCGCAGAACCAATCTGGCAA
CACTGGCAGCATAATTAACAACTACTACATGCAGCAATACCAGAACTCCA
TGGACACACAGTTGGGAGACAATGCCATCAGTGGAGGCTCCAACGAGGGC
TCCACGGACACAACTTCAACACACACAACCAACACTCAAAACAATGACTG
GTTCTCGAAGCTCGCCAGTTCAGCTTTTACCGGTCTGTTCGGTGCACTGC
TCGCCGACAAGAAGACAGAGGAAACGACACTTCTTGAGGACCGCATCCTC
ACCACCCGCAACGGGCACACCCACCTCTCGACGACCCAATCGAGTGTGGGTGT
CACATACGGGTACTCCACAGGGGAGGACCCACGTTTCTGGGCCTCAACACAT
CGGGCCTGGAGACGCGAGTGGTGCAGGCAGAGAGATTCTTCAAAAAGTTC
TTGTTTGACTGGACAACGGACAAGCCATTTGGACACCTGGAAAAGCTGGA
GCTCCCGACCGACCACAAGGGTGTCTACGGACACTTGGTGGACTCGTTCG
CCTATATGAGAAATGGCTGGGATGTTGAGGTGACCGCTGTTGGCAACCAG
TTCAACGGCGGGTGCCTCCTGGTGGCCATGGTACCTGAATGGAAGGAATTT
TACAACACGGGAGAAATACCAACTCACCCTTTTCCCGCACCAGTTTATTA
ACCCCAGAACTAACATGACTGCCCACATCGTGGTCCCCTACCTTGGTGTG
AACAGGTATGATCAGTACAAGAAGCATAAGCCCTGGACATTGGTTGTCAT
GGTCGTGTCGCCACTTACGACCACAAGCATTGGTGCGACACAAATCAAGG
TCTACGCCAACATAGCTCCGACCTATGTTCACGTGGCCGGTGAACTCCCC
TCGAAAGAGGGGATTGTCCCGGTTGCATGTGCGGACGGTTACGGAGGATT
GGTGACGACAGACCCGAAGACAGCTGACCCTGTTTATGGCATGGTGTACA
ACCCGCCTAGGACTAACTTCCCTGGGCGCTTCACCAACCTGTTGGACGTG
GCCGAAGCGTGTCCCACTTTCCTCTGCTTTGACAACGGGAAACCGTACGT
CGTCACGCGGACGGATGAACAGCGACTTTTGGCCAAGTTTGACCTTTCCC
TTGCCGCAAAACATATGTCCAACACATACCTGTCAGGGATTGCTCAGTAC
TACGCACAGTACTCTGGCACCATCAATTTGCATTTCATGTTCACAGGTTC
CACTGATTCAAAGGCCCGATACATGGTGGCCTACGTCCCACCTGGGGTGG
AGACACCACCGGACACACCTGAAAGGGCTGCCCACTGCATTCACGCTGAA
TGGGACACTGGACTAAACTCCAAATTCACTTTCTCAATCCCGTACATGTC
CGCCGCGGATTACGCGTACACAGCGTCTGACGTGGCAGAAACAACCAACGT
TACAGGGATGGGTCTGCGTCTACCAAATTACACACGGGAAGGCTGAAAAT
GACACCTTGGTCGTGTCGGCCAGCGCCGGCAAAGACTTTGAGTTGCGCCT
CCCGATTGACCCCCGCGCGCGACACCACCGCTACCGGGGAATCAGCAGACC
CGGTCACCACCGCCGTGGAGAACTACGGCGGTGAGACACAAGTCCAGAGA
CGTCACCCACACGGACGTTAGTTTCATCATGGACAGATTTGTGAAGATCGG
AACCACTAACCCAACACATGTCATTGACCTCATGCAGACTCACCAACACG
GTCTGGTGGGTGCCTTGCTGCGTGCAGCCACGTACTACTTTTCTGACCTG
GAAATTGTTGTACGGCACGAAGGCAATCTGACCTGGGTGCCCAACGGCGC
CCCTGAAGCAGCCCTGTCCAACACAGGAAACCCCACTGCCTACAACAAGG
CACCATTCACGAGACTCGCTCTCCCCTACACTGCGCCGCACCGTGTGCTG
GCAACAGTGTACAACGGGACGACAAGTACTCCGCGGCCAGTGGGCGCAC
AAGAGGCGACTTGGGGCAACTCGCGGCGCGAATCGCGGCACAGCTTCCTG
CTTCATTTAACTTCGGTGCAATCAAGGCCGACGCCATCCACGAACTTCT
GTGCGCATGAAACGGGCCGAGCTCTACTGCCCCAGACCGCTGTTGGCAAT
AGAGGTGTCTTCGCAAGACAGGTACAAGCAAAAGATCATTGCACCAGCAA
AGCAG
```

SEQ ID NO: 2 is the amino acid sequence of the mosaic FMDV-VP4.2.1 capsid:

```
GAGQSSPATGSQNQSGNTGSIINNYYMQQYQNSMDTQLGDNAISGGSNEG
STDTTSTHTTNTQNNDWFSKLASSAFTGLFGALLADKKTEETTLLEDRIL
TTRNGHTTSTTQSSVGVTYGYSTGEDHVSGPNTSGLETRVVQAERFFKKF
LFDWTTDKPFGHLEKLELPTDHKGVYGHLVDSFAYMRNGWDVEVSAVGNQ
FNGGCLLVAMVPEWKKFTTREKYQLTLFPHQFINPRTNMTAHIVVPYLGV
NRYDQYKKHKPWTLVVMVVSPLTTTSIGATQIKVYANIAPTYVHVAGELP
SKEGIVPVACADGYGGLVTTDPKTADPVYGMVYNPPRTNFPGRFTNLLDV
AEACPTFLCFDNGKPYVVTRTDEQRLLAKFDLSLAAKHMSNTYLSGIAQY
YAQYSGTINLHFMFTGSTDSKARYMVAYVPPGVETPPDTPERAAHCIHAE
WDTGLNSKFTFSIPYMSAADYAYTASDTAETTNVQGWVCVYQITHGKAEN
DTLVVSASAGKDFELRLPIDPRAQTTATGESADPVTTAVENYGGETQVQR
RHHTDVSFIMDRFVKIGTTNPTHVIDLMQTHQHGLVGALLRAATYYFSDL
EIVVRHEGNLTWVPNGAPEAALSNTGNPTAYNKAPFTRLALPYTAPHRVL
ATVYNGTNKYSAASGRTRGDLGQLAARIAAQLPASFNFGAIKADAIHELL
VRMKRAELYCPRPLLAIEVSSQDRYKQKIIAPAKQ
```

SEQ ID NO: 3 is the nucleotide sequence of the mosaic FMDV-VP4.2.2 capsid:

```
GGGGCCGGCCAATCCAGTCCGGCGACCGGCTCGCAGAACCAATCTGGCAA
CACTGGCAGCATAATTAACAACTACTACATGCAGCAATACCAGAACTCCA
TGGACACACAGTTGGGAGACAATGCCATCAGTGGAGGCTCCAACGAGGGC
CCACGGACACAACTTCAACACACACAACCAACACTCAAAACAATGACTGG
TTCTCGAAGCTCGCCAGTTCAGCTTTTACCGGTCTGTTCGGTGCACTGCT
CGCCGACAAGAAGACAGAGGAAATCACACTTCTTGAGGACCGCATCCTCA
CCACCCGCAACGGGCACACCATCTCGACGACCCAATCGAGTGTGGGTGTC
ACATACGGGTACTCCACAGAGGAGGACCACGTTGCTGGGCCCAACACATC
GGGCCTGGAGACGCGAGTGGTGCAGGCAGAGAGATTCTTCAAAAAGCACT
TGTTTGACTGGACAACGGACAAGGCATTTGGACACCTGGAAAAGCTGGAG
CTCCCGACCGAACACAAGGGTGTCTACGGACACTTGGTGGACTCGTACGC
CTATATGAGAAATGGCTGGGATGTTGAGGTGACCGCTGTTGGCAACCAGT
TCAACGGCGGGTGCCTCCTGGTGGCCATGGTACCTGAATGGAAGGAATTT
ACCCCACGGGAGAAATACCAACTCACCCTTTTCCCGCACCAGTTTATTAG
CCCCAGAACTAACATGACTGCCCACATCACGGTCCCCTACCTTGGTGTGA
ACAGGTATGATCAGTACAAGCAGCATAAGCCCTGGACATTGGTTGTCATG
GTCGTGTCGCCACTTACGACCAGCAGCATTGGTGCGTCACAAATCAAGGT
CTACGCCAACATAGCTCCGACCCATGTTCACGTGGCCGGTGAACTCCCCT
CGAAAGAGGGGATTGTCCCGGTTGCATGTTCGGACGGTTACGGAGGATTG
GTGACGACAGACCCGAAGACAGCTGACCCTGCTTATGGCAAGGTGTACAA
CCCGCCTAGGACTAACTACCCTGGGCGCTTCACCAACCTGTTGGACGTGG
CCGAAGCGTGTCCCACTTTCCTCTGCTTTGACGACGGGAAACCGTACGTC
GTCACGCGGACGGATGACCAGCGACTTTTGGCCAAGTTTGACGTTTCCCT
TGCCGCAAAACATATGTCCAACACATACCTGGCAGGGCTTGCTCAGTACT
ACACACAGTACTCTGGCACCATCAATTTGCATTTCATGTTCACAGGTTCC
ACTGAGTCAAAGGCCCGATACATGGTGGCCTACATCCCACCTGGGGTGGA
GACACCACCGGACACACCTGAAAAGGCTGCCCACTGCATTCACGCTGAAT
GGGACACTGGACTAAACTCCAAATTCACTTTCTCAATCCCGTACGTATCC
GCCGCGGATTACGCGTACACAGCGTCTGACGTGGCAGAAACAACCAACGT
ACAGGGATGGGTCTGCATCTACCAAATTACACACGGGAAGGCTGAACAAG
ACACCTTGGTCGTGTCGGTTAGCGCCGGCAAAGACTTTGAGTTGCGCCTC
CCGATTGACCCCCGCACGCAGACCACCACTGCCGGGGAATCAGCAGACCC
GGTCACCACCGTGGAGAACTACGGCGGTGAGACACAAGCCCAGAGAC
GTCACCACACGGACGTTGGTTTCATCATGGACAGATTTGTGAAGATCGGA
AACACGAGCCCAACACATGTCATTGACCTCATGCAGACTCACCAACACGC
TCTGGTGGGTGCCTTGCTGCGTGCAGCCACGTACTACTTTTCTGACCTGG
AAATTGTTGTACGGCACGACGGCAATCTGACCTGGGTGCCCAACGGCGCC
CCTGTAGAAGCTCTGGCAACACCAGCAACCCCACTGCCTACCACAAGCA
ACCATTCACGAGACTCGCTCTCCCCTACACTGCGCCGCACCGTGTGCTGG
CAACAGTGTACAACGGGACGACAAGTAAGTACTCCGCCGCTGCTACAAGAGA
GGCGACTTGGGGTCTCTCGCGGCGCGAGTCGGCGCACAGCTTCCTTCTTC
ATTTAACTTCGGTGCAATCAGGGCCACCACCATCCACGAACTTCTCGTGC
GCATGAGACGGGCCGAGCTCTACTGCCCCAGACCGCTGTTGGCAGTAGAG
GTGTCTTCGCAAGACAGGCACAAGCAAAAGATCATTGCACCAGCAAGGCA
G
```

SEQ ID NO: 4 is the amino sequence of the mosaic FMDV-VP4.2.2 capsid:

```
GAGQSSPATGSQNQSGNTGSIINNYYMQQYQNSMDTQLGDNAISGGSNEGS
TDTTSTHTTNTQNNDWFSKLASSAFTGLFGALLADKKTEEITLLEDRILTT
RNGHTISTTQSSVGVTYGYSTEEDHVAGPNTSGLETRVVQAERFFKKHLFD
WTTDKAFGHLEKLELPTEHKGVYGHLVDSYAYMRNGWDVEVTAVGNQFNGG
CLLVAMVPEWKEFTPREKYQLTLFPHQFISPRTNMTAHIIVPYLGVNRYDQ
YKQHKPWTLVVMVVSPLTTSSIGASQIKVYANIAPTHVHVAGELPSKEGIV
PVACSDGYGGLVTTDPKTADPAYGKVYNPPRTNYPGRFTNLLDVAEACPTF
LCFDDGKPYVVTRTDDQRLLAKFDVSLAAKHMSNTYLAGLAQYYTQYSGTI
NLHFMFTGSTESKARYMVAYIPPGVETPPDTPEKAAHCIHAEWDTGLNSKF
TFSIPYVSAADYAYTASDVAETTNVQGWVCIYQITHGKAEQDTLVVSVSAG
KDFELRLPIDPRTQTTTAGESADPVTTVENYGGETQAQRRHHTDVGFIMD
RFVKIGNTSPTHVIDLMQTHQHALVGALLRAATYYFSDLEIVVRHDGNLTW
VPNGAPVEALANTSNPTAYHKQPFTRLALPYTAPHRVLATVYNGTSKYSAP
ATRRGDLGSLAARVAAQLPSSFNFGAIRATTIHELLVRMRRAELYCPRPLL
AVEVSSQDRHKQKIIAPARQ
```

-continued

SEQUENCES

SEQ ID NO: 5 is the nucleotide sequence of the SanDI forward primer:
AGCGGAGCATGACGGCCGTGGGACCC SEQ ID NO: 6 is the nucleotide sequence of the VP4 reverse primer:
TGTTCGGTGCACTGCTCGCCG SEQ ID NO: 7 is the nucleotide sequence of the VP4 forward primer:
TGTTCGGTGCACTGCTCGCCG SEQ ID NO: 8 is the nucleotide sequence of the NheI reverse primer:
TCAACGTCTCCGGCTAGCTTAAGCAGGTCAAAATTC

DETAILED DESCRIPTION OF THE INVENTION

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Abbreviations

BEI binary ethyleneimine
FMDV foot-and-mouth disease virus
IC infectious cDNA clone
ORF open reading frame
PFU plaque forming unit
UTR untranslated region
VP viral protein
WT wild type

Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8)

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administration: To provide or give a subject an agent, such as a therapeutic agent (e.g. a recombinant virus), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Degenerate variant: In the context of the present disclosure, a "degenerate variant" refers to a polynucleotide encoding a peptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Heterologous: A heterologous protein or polypeptide refers to a protein or polypeptide derived from a different source or species.

Immune response: A response of a cell of the immune system, such as a B-cell, T-cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: A compound, composition, or substance which is capable, under appropriate conditions, of stimulating an immune response, such as the production of antibodies or a T-cell response in an animal, including compositions that are injected or absorbed into an animal.

Immunize: To render a subject protected from an infectious disease, such as by vaccination.

Isolated: An "isolated" biological component (such as a nucleic acid molecule, protein, virus or cell) has been substantially separated or purified away from other biological components in the cell or tissue of an organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents (e.g. a mosaic polypeptide or recombinant virus disclosed herein).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide or protein: A polymer in which the monomers are amino acid residues which are joined together through amide bonds. When the amino acids are alpha-amino acids, either the L-optical isomer or the D-optical isomer can be used. The terms "polypeptide," "peptide" and "protein" are used interchangeably herein. These terms apply to amino acid polymers in which one or more amino acid residue is an artificial chemical mimetic of a corresponding naturally occurring amino acid, as well as to naturally occurring amino acid polymers and non-naturally occurring amino acid polymers. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term "purified" does not require absolute purity; rather, it is intended as a relative term. Thus, for example, a purified polypeptide, protein, nucleic acid virus, or other active compound is one that is isolated in whole or in part from naturally associated proteins and other contaminants. In certain embodiments, the term "substantially purified" refers to a polypeptide, protein, nucleic acid, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule, protein or virus is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids, proteins and viruses that have been altered solely by addition, substitution, or deletion of a portion of the natural nucleic acid molecule, protein or virus.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and C. elegans sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Subject: Living multi-cellular vertebrate organisms, a category that includes human and non-human mammals. In the some embodiments herein, the subject is a cloven-footed animal, such as, but not limited to, a cow, pig, sheep, goat, deer, antelope, water buffalo or bison.

Synthetic: Produced by artificial means in a laboratory, for example a synthetic nucleic acid or protein can be chemically synthesized in a laboratory.

Vaccine: A preparation of immunogenic material capable of stimulating an immune response, administered for the prevention, amelioration, or treatment of disease, such as an infectious disease. The immunogenic material may include, for example, attenuated or killed microorganisms (such as attenuated viruses), or antigenic proteins, peptides or DNA derived from an infectious microorganism. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Introduction

Diversity is a major problem for virus vaccine development (Gaschen et al., *Science* 296(5577):2354-2360, 2002). The "mosaic" concept for immunogen design was developed to improve the breadth of response to HIV-1 vaccines (Fischer et al., *Nat Med* 13:100-106, 2007). The method includes generating an optimized cocktail of synthetic viral protein sequences, such as for co-administration, so that maximal numbers of potential epitopes, weighted by population frequency, are presented in the vaccine (FIG. 1). HIV-1 vaccines designed by this method have shown substantial promise in animal studies (Kong et al., *J Virol* 83(5):2201-2215, 2009; Barouch et al., *Nat Med* 16(3):319-323, 2010; Santra et al., *Virology* 428(2):121-127, 2012), including protection from virulent simian-human immunodeficiency virus (SHIV) challenge (Barouch et al., *Cell* 155(3):531-539, 2013). Several human phase I trials are in progress to evaluate mosaic HIV-1 vaccines. Mosaic vaccines have shown promise for other viruses as well, including hepatitis C virus (HCV) (Yusim et al., *J Gen Virol* 91:1194-1206, 2010; Yusim et al., *Clin Vaccine Immunol* 20(2):302-305, 2013), filoviruses (e.g., Ebola virus, Marburg virus) (Fenimore et al., *PLoS ONE* 7(10):e44769, 2012), and influenza virus (Kamlangdee et al., *J Virol* 88(22):13300-13309, 2014). The immunogens designed by this method are optimized for linear epitope coverage, but in many cases preserve conformational epitopes.

The FMDV mosaic polypeptide and nucleic acid compositions disclosed herein provide higher levels of T-cell epitope coverage compared to natural FMDV polypeptides and consensus FMDV sequences, while minimizing the occurrence of unnatural and rare epitopes.

Overview of Several Embodiments

Disclosed herein are synthetic FMDV mosaic polypeptides that have greater T-cell epitope coverage than naturally occurring FMDV polypeptides. The synthetic FMDV mosaic polypeptides incorporate natural virus variability and include common FMDV epitopes, but exclude rare FMDV epitopes. When included as part of an FMDV genome, the mosaic polypeptides permit viral replication and virus assembly into structures that are highly similar or identical to native FMDV particles. The mosaic polypeptide and nucleic acid compositions disclosed herein can be used to elicit immune responses that provide protection against a broad range of serotype A FMDV strains.

Provided herein are synthetic FMDV polypeptides having an amino acid sequence at least 80%, at least 85%, at least 90%, at least 95%, at least 96%, at least 97%, at least 98% or at least 99% identical to mosaic polypeptide VP4.2.1 (SEQ ID NO: 2) or mosaic polypeptide VP4.2.2 (SEQ ID NO: 4). In some embodiments, the synthetic FMDV polypeptide includes the amino acid sequence of SEQ ID NO: 2 or SEQ ID NO: 4. In specific examples, the synthetic FMDV polypeptide consists of the amino acid sequence of SEQ ID NO: 2 or SEQ ID NO: 4.

Recombinant FMDV that include mosaic polypeptides are also provided herein. In some embodiments, the recombinant FMDV includes a synthetic FMDV polypeptide having an amino acid sequence at least 80%, at least 85%, at least 90%, at least 95%, at least 96%, at least 97%, at least 98% or at least 99% identical to mosaic polypeptide VP4.2.1 (SEQ ID NO: 2) or mosaic polypeptide VP4.2.2 (SEQ ID NO: 4). In some embodiments, the recombinant FMDV includes a synthetic polypeptide comprising the amino acid sequence of SEQ ID NO: 2 or SEQ ID NO: 4. In specific examples, the recombinant FMDV includes a synthetic FMDV polypeptide consisting of the amino acid sequence of SEQ ID NO: 2 or SEQ ID NO: 4. In some embodiments, the recombinant FMDV include the FMDV L, VP4, P2 and P3 proteins from a wild-type FMDV strain. In specific non-limiting examples, the wild-type FMDV strain is $A_{24}$ Cruzeiro.

Further provided herein are nucleic acid molecules encoding mosaic FMDV polypeptides. In some embodiments, the nucleic acid encodes a synthetic FMDV polypeptide having an amino acid sequence at least 80%, at least 85%, at least 90%, at least 95%, at least 96%, at least 97%, at least 98% or at least 99% identical to mosaic polypeptide VP4.2.1 (SEQ ID NO: 2) or mosaic polypeptide VP4.2.2 (SEQ ID NO: 4). In some embodiments, the nucleic acid molecule encodes a synthetic FMDV polypeptide comprising the amino acid sequence of SEQ ID NO: 2 or SEQ ID NO: 4. In specific examples, the nucleic acid molecule encodes a synthetic FMDV polypeptide consisting of the amino acid sequence of SEQ ID NO: 2 or SEQ ID NO: 4. In some embodiments, the nucleic acid molecule has a nucleotide sequence at least 80%, at least 85%, at least 90%, at least 95%, at least 96%, at least 97%, at least 98% or at least 99% identical to SEQ ID NO: 1 or SEQ ID NO: 3. In some examples, the nucleic acid molecule has a nucleotide sequence comprising SEQ ID NO: 1 or SEQ ID NO: 3. In particular non-limiting examples, the nucleic acid molecule has a nucleotide sequence consisting of SEQ ID NO: 1 or SEQ ID NO: 3.

Vectors comprising the mosaic FMDV polypeptide-encoding nucleic acid molecules are also provided by the present disclosure. In some embodiments, the vector further includes coding sequences for FMDV L, VP4, P2 and P3 proteins, whereupon transfection of the vector into a permissive host cell, infectious FMDV is produced. In some examples, the FMDV L, VP4, P2 and P3 proteins have the amino acid sequence of a wild-type FMDV. In specific non-limiting examples, the wild-type FMDV is $A_{24}$ Cruzeiro.

Also provided herein are compositions that include at least one mosaic FMDV polypeptide, at least one recombinant FMDV, or at least one mosaic FMDV polypeptide encoding nucleic acid or at least one vector disclosed herein.

In some embodiments, provided is a composition that includes a mosaic FMDV polypeptide having an amino acid sequence at least 80%, at least 85%, at least 90%, at least 95%, at least 96%, at least 97%, at least 98% or at least 99% identical to mosaic polypeptide VP4.2.1 (SEQ ID NO: 2), comprising SEQ ID NO: 2, or consisting of SEQ ID NO; 2, and a pharmaceutically acceptable carrier. In some embodiments, provided is a composition that includes a mosaic FMDV polypeptide having an amino acid sequence at least 80%, at least 85%, at least 90%, at least 95%, at least 96%, at least 97%, at least 98% or at least 99% identical to mosaic polypeptide VP4.2.2 (SEQ ID NO: 4), comprising SEQ ID NO: 4, or consisting of SEQ ID NO: 4, and a pharmaceutically acceptable carrier. In some examples, the composition includes a mosaic FMDV polypeptide comprising or consisting of SEQ ID NO: 2 (or at least 80%, at least 85%, at least 90%, at least 95%, at least 96%, at least 97%, at least 98% or at least 99% identical to SEQ ID NO: 2); a mosaic FMDV polypeptide comprising or consisting of SEQ ID NO: 4 (or at least 80%, at least 85%, at least 90%, at least 95%, at least 96%, at least 97%, at least 98% or at least 99% identical to SEQ ID NO: 4); and a pharmaceutically acceptable carrier.

In some embodiments, provided is a composition that includes a recombinant FMDV that comprises a mosaic FMDV polypeptide with an amino acid sequence comprising or consisting of SEQ ID NO: 2 (or at least 80%, at least 85%, at least 90%, at least 95%, at least 96%, at least 97%, at least 98% or at least 99% identical to SEQ ID NO: 2), and a pharmaceutically acceptable carrier. In some embodiments, provided is a composition that includes a recombinant FMDV that comprises a mosaic FMDV polypeptide with an amino acid sequence comprising or consisting of SEQ ID NO: 4 (or at least 80%, at least 85%, at least 90%, at least 95%, at least 96%, at least 97%, at least 98% or at least 99% identical to SEQ ID NO: 4), and a pharmaceutically acceptable carrier. In some examples, the composition includes a first recombinant FMDV comprising a synthetic polypeptide having the amino acid sequence of SEQ ID NO: 2 (or at least 80%, at least 85%, at least 90%, at least 95%, at least 96%, at least 97%, at least 98% or at least 99% identical to SEQ ID NO: 2), a second recombinant FMDV comprising a synthetic polypeptide having the amino acid sequence of SEQ ID NO: 4 (or at least 80%, at least 85%, at least 90%, at least 95%, at least 96%, at least 97%, at least 98% or at least 99% identical to SEQ ID NO: 4), and a pharmaceutically acceptable carrier.

Further provided herein are compositions that include a vector that includes a mosaic FMDV polypeptide-encoding nucleic acid molecule disclosed herein. In some embodiments, the composition includes a vector comprising a nucleic acid molecule having the sequence of SEQ ID NO: 1 (or at least 80%, at least 85%, at least 90%, at least 95%, at least 96%, at least 97%, at least 98% or at least 99% identical to SEQ ID NO: 1), and a pharmaceutically acceptable carrier. In some embodiments, the composition includes a vector comprising a nucleic acid molecule having the sequence of SEQ ID NO: 3 (or at least 80%, at least 85%, at least 90%, at least 95%, at least 96%, at least 97%, at least 98% or at least 99% identical to SEQ ID NO: 3), and a pharmaceutically acceptable carrier. In some examples, the composition includes a first vector comprising a nucleic acid molecule having the sequence of SEQ ID NO: 1 (or at least 80%, at least 85%, at least 90%, at least 95%, at least 96%, at least 97%, at least 98% or at least 99% identical to SEQ ID NO: 1); a second vector comprising a nucleic acid molecule having the sequence of SEQ ID NO: 3 (or at least 80%, at least 85%, at least 90%, at least 95%, at least 96%, at least 97%, at least 98% or at least 99% identical to SEQ ID NO: 3); and a pharmaceutically acceptable carrier.

In some embodiments herein, the composition further includes an adjuvant.

Further provided herein are methods of eliciting an immune response against serotype A FMDV in a subject. In some embodiments, the method includes administering to the subject a synthetic FMDV mosaic polypeptide, a recombinant FMDV, a nucleic acid molecule, a vector, or a composition disclosed herein. In some examples, the subject is a cow.

Also provided herein are methods of immunizing a subject against serotype A FMDV. In some embodiments, the method includes administering to the subject a synthetic FMDV mosaic polypeptide, a recombinant FMDV, a nucleic acid molecule, a vector, or a composition disclosed herein. In some examples in which the recombinant FMDV is administered, the recombinant FMDV is inactivated (such as with BEI) prior to administration.

In some embodiments of the methods provided herein, the subject is a cloven-footed animal. In some examples, the cloven-footed animal is a cow, pig, sheep, goat, deer, antelope, water buffalo or bison.

Administration of Mosaic FMDV Vaccine Compositions

The FMDV mosaic polypeptide and polynucleotide compositions described herein can be administered to a subject using any suitable delivery means. For example, FMDV polynucleotides or polypeptides can be administered parenterally, by injection, subcutaneously, intramuscularly, transdermally or transcutaneously. Certain adjuvants, for example LTK63, LTR72 or PLG formulations, can be administered intranasally or orally. Additional formulations that are suitable for other modes of administration include suppositories. For suppositories, traditional binders and carriers can include, for example, polyalkylene glycols or triglycerides; such suppositories can be formed from mixtures containing the active ingredient in the range of 0.5% to 10%, such as 1%-2%. Other oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, such as 25%-70%.

The FMDV mosaic vaccines disclosed herein are typically prepared as injectables, either as liquid solutions or suspensions. Solid forms suitable for solution or suspension in liquid prior to injection may also be prepared. Such preparations can also be emulsified, or encapsulated in liposomes. In some instances, the vaccine also includes a pharmaceutically acceptable carrier. Pharmaceutically acceptable carriers are well known to those in the art, and include without limitation large, slowly metabolized macromolecules, such as proteins, polysaccharides, functionalized sepharose, agarose, cellulose, cellulose beads and the like, polylactic acids, polyglycolic acids, polymeric amino acids such as polyglutamic acid, polylysine, and the like.

The FMDV mosaic vaccines disclosed herein can be formulated into an immunogenic compound as neutral or salt forms. Pharmaceutically acceptable salts include the acid addition salts (formed with free amino groups of the peptide) and those formed with inorganic acids such as, for example, hydrochloric or phosphoric acids, or organic acids such as acetic, oxalic, tartaric, maleic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Vaccine compositions can also contain liquids or excipients, such as water, saline, glycerol, dextrose, ethanol, or the like, singly or in combination, as well as substances such as wetting agents, emulsifying agents, or pH buffering agents. Liposomes can also be used as a carrier for a composition disclosed herein.

Various co-stimulatory molecules can be included in the vaccine preparation or delivery protocol. These molecules can improve immunogen presentation to lymphocytes, and include such proteins as B7-1 or B7-2, and cytokines such as GM-CSF, IL-2, and IL-12. Optionally, adjuvants can also be included in a composition. Various adjuvants may be used, including (1) aluminum salts (alum), such as aluminum hydroxide, aluminum phosphate, or aluminum sulfate; (2) oil-in-water emulsion formulations (with or without other specific immunostimulating agents such as muramyl peptides or bacterial cell wall components); (3) saponin adjuvants, or particles generated therefrom such as ISCOMs (immunostimulating complexes); (4) Complete Freund's Adjuvant (CFA) and Incomplete Freund's Adjuvant (IFA); (5) cytokines, such as interleukins (for example, IL-1, IL-2, IL-4, IL-5, IL-6, IL-7, or IL-12), interferons (for example, gamma interferon), macrophage colony stimulating factor (M-CSF), or tumor necrosis factor (TNF); (6) detoxified mutants of a bacterial ADP-ribosylating toxin such as a cholera toxin (CT), a pertussis toxin (PT), or an *E. coli* heat-labile toxin (LT); (7) other substances that act as immunostimulating agents to enhance the effectiveness of the composition; and (8) microparticles with adsorbed macromolecules.

The FMDV mosaic vaccine compositions disclosed herein can be administered in a manner compatible with the dosage formulation, and in such amount as will be prophylactically and/or therapeutically effective. The quantity to be administered depends on the subject to be treated, the capacity of the subject's immune system, and the degree of protection desired. Precise amounts of active ingredient required to be administered may depend on the judgment of the practitioner and can be specific to each subject.

Vaccine formulations can be introduced in a single dose schedule, or in a multiple dose schedule. A multiple dose schedule is one in which a primary course of vaccination can be with 1-10 separate doses, followed by other doses given at subsequent time intervals required to maintain and or reinforce the immune response, for example, at 1-4 months for a second dose, and if needed, a subsequent dose(s) after several months.

The course of administration can include polynucleotides and polypeptides, together or sequentially (for example, priming with a polynucleotide composition and boosting with a polypeptide composition). The dosage regimen will also, at least in part, be determined by the need of the individual and be dependent upon the judgment of the practitioner.

Nucleic acid molecules and vectors comprising expressible polynucleotides encoding FMDV mosaic proteins can be formulated and utilized as DNA vaccine preparations. Such FMDV mosaic DNA vaccines can be used to activate FMDV-specific T cells, using standard gene delivery protocols. Methods for gene delivery are known in the art (see, for example, U.S. Pat. Nos. 5,399,346, 5,580,859, 5,589,466, incorporated by reference herein in their entireties). Genes can be delivered either directly to the vertebrate subject or, alternatively, delivered ex vivo, to cells derived from the subject and the cells reimplanted in the subject. For example, the constructs can be delivered as plasmid DNA, or viral vector DNA.

DNA vaccines can be introduced by a number of different methods, including by injection of DNA in saline, using a standard hypodermic needle. Injection in saline is typically conducted intramuscularly in skeletal muscle, or intradermally, with DNA being delivered to the extracellular spaces. This can be assisted by electroporation, by temporarily damaging muscle fibers with myotoxins such as bupivacaine or by using hypertonic solutions of saline or sucrose. Immune responses to this method of delivery can be affected by many factors, including needle type, needle alignment, speed of injection, volume of injection, muscle type, and age, sex and physiological condition of the individual being injected.

Gene gun delivery ballistically accelerates plasmid DNA (pDNA) that has been adsorbed onto gold or tungsten microparticles into the target cells, using compressed helium as an accelerant. Alternative delivery methods include aerosol instillation of naked DNA on mucosal surfaces, such as the nasal and lung mucosa, and topical administration of pDNA to the eye and vaginal mucosa. Mucosal surface delivery has also been achieved using cationic liposome-DNA preparations, biodegradable microspheres, attenuated Shigella or Listeria vectors for oral administration to the intestinal mucosa, and recombinant virus vectors, such as adenovirus vectors.

The method of delivery determines the dose of DNA required to raise an effective immune response. Saline injections require variable amounts of DNA, from 10 μg-1 mg, whereas gene gun deliveries require 100 to 1000 times less DNA than intramuscular saline injection to raise an effective immune response. Generally, 0.2 μg to 20 μg are required, although quantities as low as 16 ng have been utilized. Saline injections require more DNA because the DNA is delivered to the extracellular spaces of the target tissue (typically, muscle tissue), where physical barriers such as the basal lamina and large amounts of connective tissue must be overcome before it is taken up by the cells, while gene gun deliveries bombard DNA directly into the cells.

FMDV mosaic nucleic acid vaccines can be packaged in liposomes prior to delivery to cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid.

Liposomal preparations for use with the disclosed FMDV vaccines include cationic (positively charged), anionic (negatively charged) and neutral preparations.

The FMDV mosaic nucleic acid vaccines can also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG (see, for example, Jeffery et al., *Pharm Res* 10:362-368, 1993).

Assessing Efficacy of FMDV Mosaic Vaccines

The ability of a particular mosaic protein or vaccine composition to stimulate a cell-mediated immunological response can be determined by any one of a number of assays, such as by lymphoproliferation (lymphocyte activation) assays, cytotoxic T lymphocyte (CTL) assays, or by assaying for T-lymphocytes specific for the antigen in a sensitized subject. Such assays are well known in the art (Erickson et al., *J Immunol* 151:4189-4199, 1993; Doe et al., *Eur J Immunol* 24:2369-2376, 1994). Thus, an immunological response can be one that stimulates the production of CTLs and/or the production or activation of helper T-cells. The antigen of interest can also elicit an antibody-mediated immune response that is important for the induction of protective immunity. Such assays are well described in the OIE manual (Manual of diagnostic test and vaccines for terrestrial animals, 2004 (5$^{th}$ edition)), Office International des Epizooties, Paris (2004), and in the literature (e.g. Tekleghiorghis et al., *Clin Vaccine Immunol* 21(5): 674-683, 2014). Hence, an immunological response may include one or more of the following effects: the production of antibodies by B-cells and/or the activation of suppressor T-cells.

Various means for estimating or actually measuring the protective immune response generated by an FMDV mosaic vaccine preparation disclosed herein can be utilized, including without limitation, in silico analytical methods designed to determine the degree of T-cell epitope coverage provided by a particular mosaic protein or combination thereof, and in vivo methods of evaluating the FMDV mosaic vaccine preparations in animals, such as cattle.

Epitopes recognized by a T cell receptor on an FMDV-activated T cell can be identified by, for example, a $^{51}$Cr release assay or by a lymphoproliferation assay, as is well known in the art. In a $^{51}$Cr release assay, target cells that display the epitope of interest are prepared, for instance by cloning a polynucleotide encoding the epitope into an expression vector and transforming the expression vector into the target cells. Target cells are incubated with $^{51}$Cr for labeling and then mixed with subject-derived T cells, after which the cytolytic activity of T cells is measured by the release of $^{51}$Cr-bound protein into the medium.

The following examples are provided to illustrate certain particular features and/or embodiments. These examples should not be construed to limit the disclosure to the particular features or embodiments described.

EXAMPLES

Example 1: Vaccine Immunogen Design and Construction

Mosaic cocktails of 1, 2, and 3 sequences were constructed for varying sets of serotype A FMDV natural-sequence data sets. FMDV capsid sequences were retrieved from the GENBANK™ database maintained by the National Center for Biotechnology Information (NCBI), aligned to one another by standard methods (Edgar, *BMC Bioinformatics* 5:113, 2004; Katoh et al., *Nucleic Acids Res* 33(2): 511-518, 2005; Larsson, *Bioinformatics* 30(22):3276-3278, 2014) and used as input for the mosaic design web tool (Thurmond et al., *Bioinformatics* 24(14):1639-1640, 2008), which was based on Fischer et al. (*Nat Med* 13:100-106, 2007). The resulting amino-acid sequences were inspected, and checked for breadth of coverage. Mosaic nucleic-acid coding-sequences were derived by applying base changes to the FMDV A$_{24}$ Cruzeiro strain sequence so that the amino acids encoded by the new sequence matched the mosaic sequences.

Figure 2A:
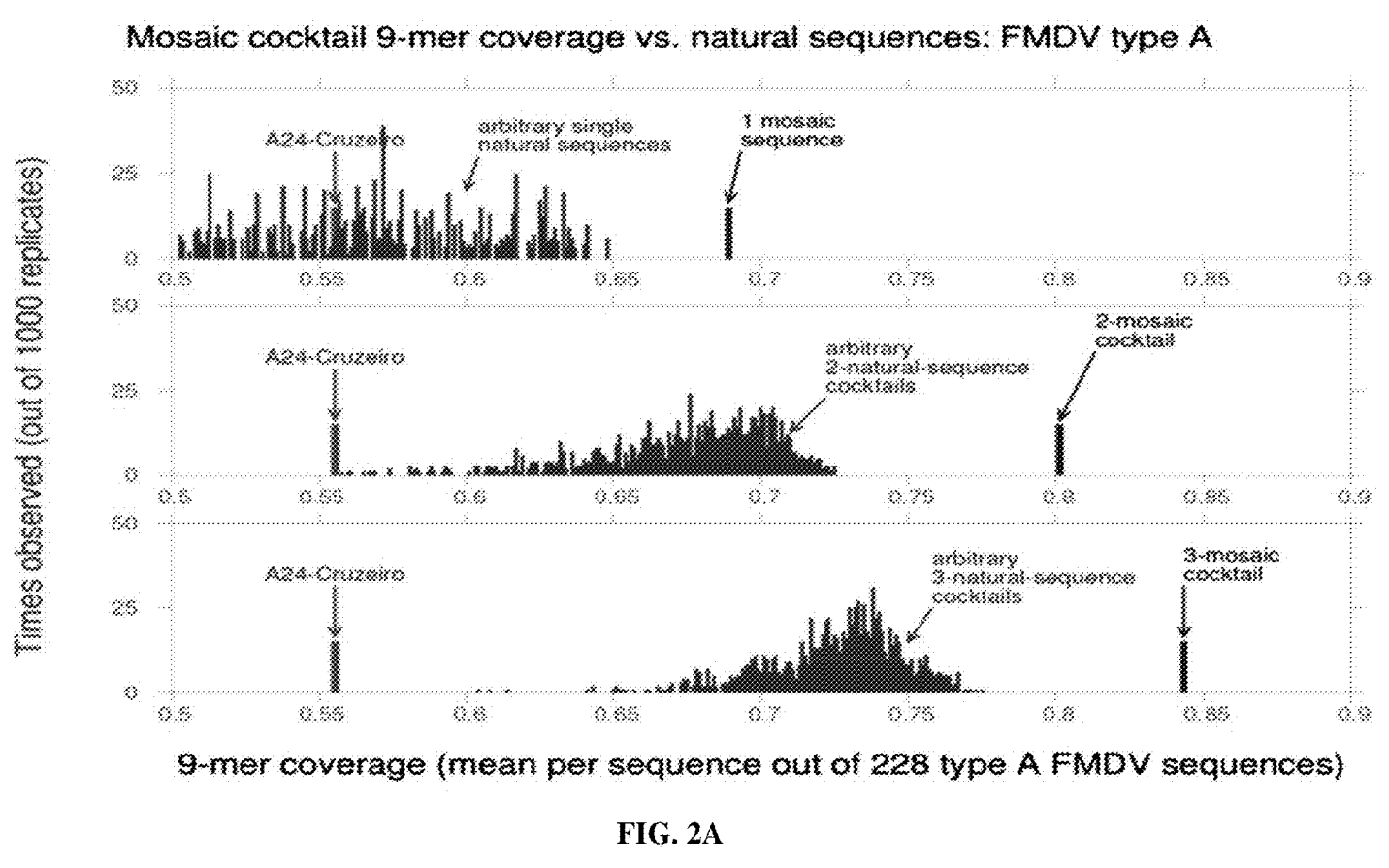
Figure 2B:
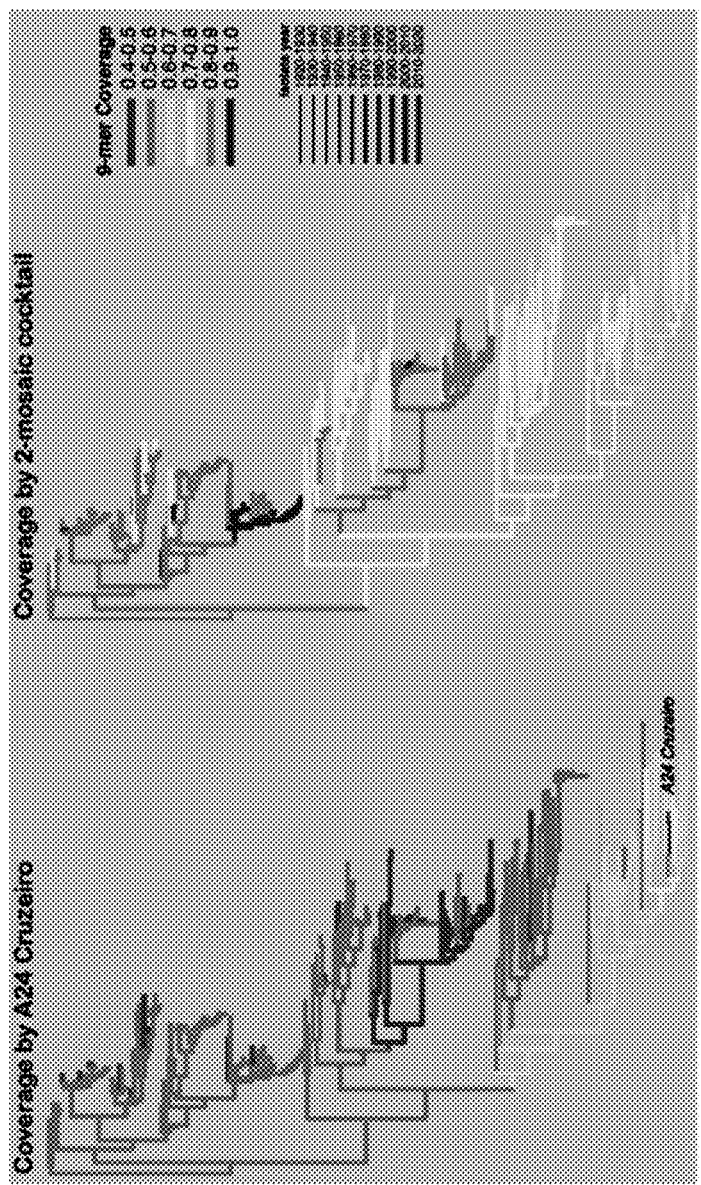
Figure 2C:
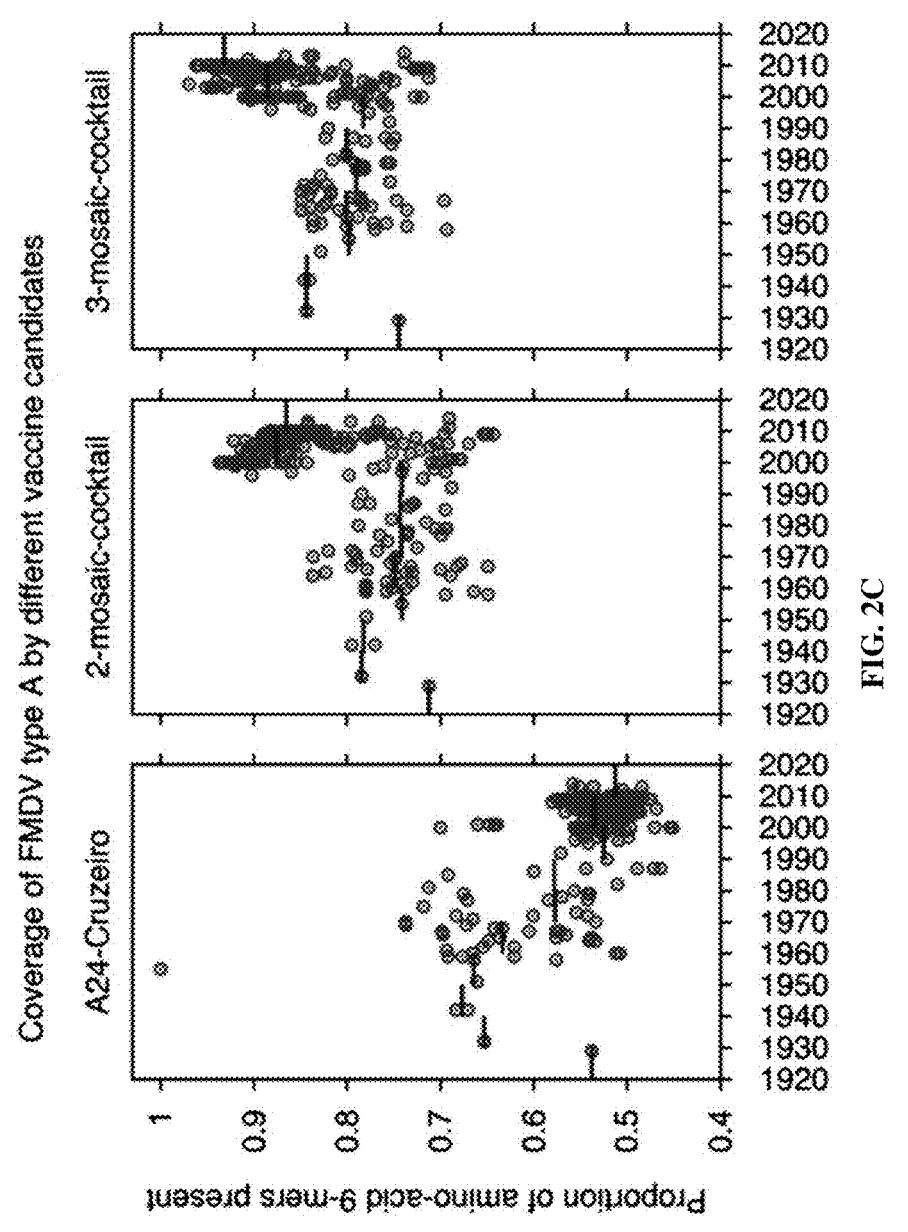

Coverage comparisons showed substantial increases between 1- and 2-sequence cocktails, with a reduced increase between 2- and 3-sequence cocktails. Therefore, additional studies proceeded with 2-sequence cocktail. The advantage of using mosaic proteins in terms of epitope coverage was striking. From a vaccinological perspective, the cocktails were far superior to natural sequences or natural-sequence cocktails (FIG. 2A). Furthermore, they had broad coverage of phylogenetic diversity (FIG. 2B), and had excellent coverage of more recent FMDV isolates (FIG. 2C). The nucleotide sequences of the mosaic vaccines were synthesized commercially, and cloned into a cDNA construct based on the A$_{24}$ Cruzeiro backbone (FIG. 4), as described in Example 2. Mosaic sequences were used for the VP2, VP3, and VP1 genes, with the remainder of the genome (5' UTR, leader sequence, VP4, and the non-structural proteins) derived from the A$_{24}$ backbone. These cDNA constructs were propagated in bovine tissue culture for several passages until infectious virus was recovered (FIG. 3).

Example 2: Cloning and Propagation of Mosaic Viruses

Figure 4:
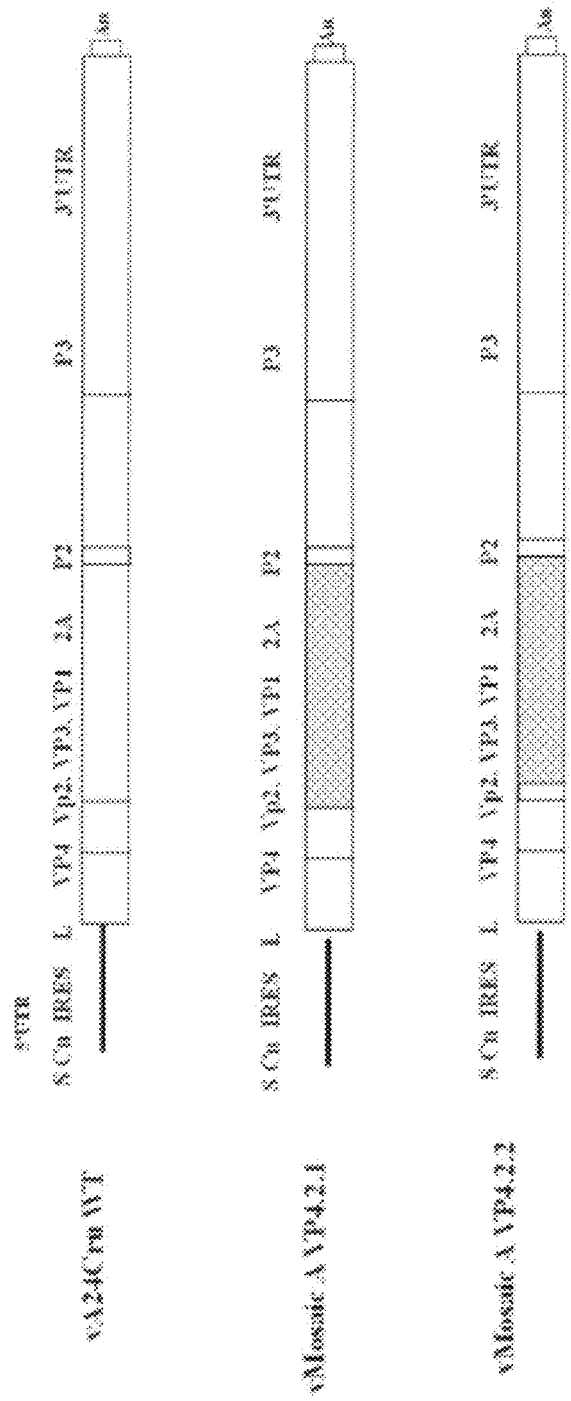
FIG. 4 shows the derivation of type A mosaic FMDV vaccines. Shown are diagrams of the FMDV genome organization and type A mosaic FMDV mutants. The basic FMDV genome organization is shown depicting the locations of proteins encoded by the viral open reading frame (ORF) and elements encoded in the 5' and 3' untranslated region (UTR). Mosaic mutant viruses were generated by DNA synthesis using as a backbone the full-length clone pA$_{24}$Cru of the FMDV outbreak strain A$_{24}$ Cruzeiro described in Rieder et al. (*J Virol.* 79:12989-12998, 2005).

A full-length infectious cDNA clone (IC) of the outbreak strain A24 Cruzeiro (pA24Cru, Rieder et al., *J Virol* 79(2): 12989-12998, 2005) was used as a template. The capsid-coding region of A24 Cruzeiro was substituted with the corresponding mosaic capsid sequences. Mosaic P1-2A sequences were synthesized by Bio Basic Canada Inc. Two successive PCR reactions were used to generate mosaic viruses comprised of VP4 and 2A from wild type FMDV A$_{24}$ Cruzeiro and VP2-VP3-VP1 from the mosaic designs. In the first PCR, the SanDI forward primer AGCGGAGCAT-GACGGCCGTGGGACCC (SEQ ID NO: 5) and the VP4 reverse primer TGTTCGGTGCACTGCTCGCCG (SEQ ID NO: 6) were used to amplify a 5'UTR-VP4 fragment from wild type FMDV A$_{24}$ Cruzeiro and the VP4 forward primer TGTTCGGTGCACTGCTCGCCG (SEQ ID NO: 7) and the NheI reverse primer TCAACGTCTCCGGCTAGCT-TAAGCAGGTCAAAATTC (SEQ ID NO: 8) were used to generate the mosaic VP2-VP3-VP1-2A PCR fragment of the mosaic 2.1 and 2.2 constructs. Then these two fragments were joined by end-overlapping PCR reaction. The amplicons were gel extracted and cloned in wild type (WT) infectious cDNA clone DNA plasmid (pA$_{24}$ WT) using the SanDI and NheI restriction sites present in 5'UTR and 2A coding region, respectively (FIG. 4). The sequences of mosaic virus VP4.2.1 (SEQ ID NO: 1) and VP4.2.2 (SEQ ID NO: 3) were verified by sequencing. An alignment of the VP4.2.1 and VP4.2.2 capsid protein sequences with parental FMDV A24 Cruzeiro and FMDV type O 1 BFS capsid is shown in FIGS. 5A-5B.

The mosaic virus cDNA clones were linearized by SwaI enzyme digestion and RNA transcripts representing the positive-sense genome of the virus were generated by MEGASCRIPT™ Kit (Ambion) following the manufacturer's instructions. The contaminants from the RNA transcription reaction were removed using RNEASY™ kit viral RNA purification following the manufacturer's instructions. Approximately 10 µg RNA was used for electroporation of freshly grown (log phase) BHK-21 cells. The samples were frozen after overnight incubation and virus passage was continued using ⅒$^{th}$ of the inoculum for the next passage. After recording cytopathic effect, a large batch of each mosaic virus was produced and a plaque assay was conducted as described previously (Rieder et al., *J Virol* 67(9): 5139-5145, 1993) for growth characterization and comparison of these viruses with WT FMDV A24 Cruzeiro. Briefly, serial dilutions of virus were adsorbed on BHK-21 cell monolayers then a 0.6% gum tragacanth overlay was added and incubated for 48 hours at 37° C. Plates were fixed, stained with crystal violet (0.3% in Histochoice; Amresco, Solon, Ohio), and the plaques were counted. Titers were expressed as plaque forming units per milliliter (PFU/ml) and performed in duplicates (FIG. 3).

Example 3: Virus Neutralization Titers and r1 Value

The two mosaic viruses (VP4.2.1 and VP4.2.2) were tested for antigenic coverage by calculating their ability to be neutralized by bovine serum from either vaccinated or FMDV-convalescent animals. Neutralizing titers are reported as the reciprocal of the last serum dilution to neutralize 100 tissue culture infectious dose of homologous FMDV in 50% of the wells (TCID)$_{50}$, as previously described (Rweyemamu et al., *J Hyg* (Lond) 81(1):107-123, 1978). One-way antigenic relations (r1-values) of mosaic viruses relative to A24 FMDV WT parental virus were calculated as the ratio between the heterologous and homologous serum titers and were interpreted as described by Samuel et al. (*Vaccine* 8(4):390-396, 1990). Virus neutralization was also performed for a number of heterologous type A FMDVs using the sera from animals vaccinated with VP4.2.1 and VP4.2.2 mosaic vaccine and r1 values were calculated to infer antigenic relationship between the vaccine and target virus.

Example 4: Antigen Production and Vaccine Formulation

BHK-21 monolayers were infected with the A$_{24}$ WT and mosaic VP4.2.1 and VP4.2.1 viruses. After observing full cytopathic effect, virus was released from cells by freeze-thaw. A brief centrifugation at 8000 g at 4° C. in a SOR-VALL™ centrifuge was performed to rid the vaccine antigens of cell debris. Supernatants containing vaccine antigens were inactivated with 5 mM BEI, pH=8.0±0.2 for 24 hours at 25° C. The inactivated antigens were then concentrated and partially purified with 8% polyethylene glycol 8000. The vaccines were prepared as water-in-oil-in-water (WOW) emulsion with Montanide ISA 201 VG (Seppic, Paris, France) according to the manufacturer's instructions. Briefly, the oil adjuvant was mixed into the aqueous antigen phase (50:50) at 30° C. for 15 minutes and stored at 4° C. for 24 hours, followed by another brief mixing cycle for 10 minutes. The integrity of 140S particles (Grubman et al., J. Virol., (1985) 56:120-26) and antigen concentration present in the experimental vaccines (15 µg/dose of chemically inactivated antigen) were determined by 15 to 45% sucrose density gradient fractionation and recording the absorbance of fractions at 259 nM and transmission electron microscopy (TEM) of uranyl acetate stained 140S preps.

Example 5: Animal Challenge

The FMDV mosaic viruses VP4.2.1 and VP4.2.2 were tested in cattle for the ability to provide protection against wild-type virus challenge. In this study, 21 cattle were used in three treatment arms to evaluate efficacy of the vaccine.

The study included paired placebo/vaccine animals for each of three distinct serotype A FMDV challenge viruses: A24 Cruzeiro (1995), wild-type isolate A (Saudi Arabia 95; A/Sau/16/95; GenBank Accession No. EU553874) and wild-type isolate B (Iran-05; A/IRN/1/2005; GenBank Accession No. EF208769). Animals were administered the FMDV mosaic vaccine (BEI inactivated proteins derived from the VP4.2.1 and VP4.2.2 mosaic viruses as a 10 μg/2 mL dose by the intramuscular route in the right and left neck, respectively) or a placebo; 21 days later, animals in one group were challenged with A24 Cruzeiro, and animals in the two other groups received a second immunization ("boost"). Fourteen days post-boost, the remaining animals were challenged with FMDV A Saudi Arabia 95 or FMDV A Iran-05. All challenges were intradermolingual with $1 \times 10^4$ bovine tongue infectious dose 50 ($BTID_{50}$) of challenge virus.

The challenge material (FMDV serotypes A24 Cruzeiro; FMDV A Saudi Arabia 95; FMDV A Iran-05). Virus Stocks were diluted in DMEM/1× antibiotics to a final concentration of $1 \times 10^4$ $BID_{50}/0.4$ ml. At 14 days post-vaccination, or post-boost, each animal received an intradermal lingual (IDL) inoculation of challenge virus by inoculation of 0.1 ml in each of four sites (0.4 ml total/animal). Vaccination, boost and challenge schedules are shown in Table 1.

ing FMDV challenge was defined as rectal temperature ≥103.5° F. at any time post-challenge (days 1-10 post-challenge). For each treatment group, protection against fever was calculated according to the formula: (number of fever negative)/(number of challenged cattle)×100%.

Antibody Titers

Antibody titers to FMDV serotypes A24 Cruzeiro, A Saudi Arabia 95, and A Iran-05 were determined by virus neutralization on serum samples collected on Days 0, 7, 14, 22, 29, 36, 43, and 50. FMDV serum virus neutralization (SVN) antibody titers were determined by a constant virus decreasing serum neutralization assay in BHK-21 cell cultures using 100-150 $TCID_{50}$ of FMDV serotypes A24 Cruzeiro, A Saudi Arabia 95, or A Iran-05. SVN titers were calculated by using the Spearman-Karber method based on cytopathic effect (CPE). The assay lower limit of detection was $0.6 \log_{10}$.

For each treatment group, individual SVN titers and treatment group mean SVN titer (geometric mean titer [GMT])±standard deviation (S.D.) to FMDV serotypes A24 Cruzeiro, A Saudi Arabia 95, and A Iran-05 were determined for each day that sera were collected. All cattle were FMDV SVN negative prior to vaccination and all controls were FMDV SVN negative prior to challenge.

TABLE 1

Summary of Design

| Treatment group | Investigational Veterinary Product and Dose | N | Challenge Virus | Route of IVP Administration; Dose volume | Frequency |
|---|---|---|---|---|---|
| T01 | Placebo vaccine (PBS) | 3 | FMDV A24 Cruzeiro | IM; 2.2 ml | Once; D0 |
| T02 | Mosaic Bivalent VP4.2.1/VP4.2.2; Right Neck: (VP4.2.1 - 10 μg). Left Neck: (VP4.2.2 - 10 μg). | 4 | | IM; 2.2 ml | Once; D0 |
| T03 | Placebo vaccine (PBS) | 3 | FMDV A Saudi Arabia 95 | IM; 2.2 ml | Once; D0 |
| T04 | Mosaic Bivalent VP4.2.1/VP4.2.2; Right Neck-D0; left neck-D22 (VP4.2.1 - 10 μg). Left Neck D0; right neck-D22 (VP4.2.2 - 10 μg). | 4 | | IM; 2.2 ml | Twice; D0 and D22. |
| T05 | Placebo vaccine (PBS) | 3 | FMDV A Iran-05 | IM; 2.2 ml | Once; D0 |
| T06 | Mosaic Bivalent VP4.2.1/VP4.2.2; Right Neck-D0; left neck-D22 (VP4.2.1 - 10 μg). Left Neck D0; right neck-D22 (VP4.2.2 - 10 μg). | 4 | | IM; 2.2 ml | Twice; D0 and D22 |

On Day 0, baseline serum samples from each animal were collected. All calves received their respective vaccine, as indicated in Table 1. On 3, 7, 10, and 14 days post-challenge (dpc), all cattle were sedated and examined for clinical signs of FMD generalized disease (pedal lesions). Clinical scoring of pedal lesions was conducted according to a standard clinical scoring system (negative=no pedal vesicular lesions observed; positive=one or more pedal vesicular lesions observed; number of lesion-positive feet and the presence or absence of tongue lesions was also recorded). Fever follow-

FMDV ELISA

The PrioCHECK® FMDV NS ELISA (ThermoFisher) was used to detect antibodies to FMDV 3ABC nonstructural proteins, according to manufacturer's instructions. A sample was considered positive if the percent inhibition was ≥50%.

Virus Isolation

Plasma samples from all cattle collected on 0-5 dpc were tested. Undiluted samples (20 μl) were added to single wells of 24-well plates containing LFBK $α_vβ_6$ cell monolayers. This cell line has been shown to be more permissive for FMDV replication compared to the parental LFBK cell line that is most commonly used for FMDV isolation. Wells (pass 1) were scored for CPE after 3-4 days. Any wells without CPE were further tested by preparing a cell lysate from each negative well and subsequent inoculation (20 μl) onto 24-well plates containing fresh LFBK $\alpha_v\beta_6$ cell monolayers. Wells (pass 2) were scored for CPE after 3-4 days and any wells without CPE were further tested as above by inoculation onto fresh cells. Wells (pass 3) were scored for CPE after 3-4 days. A similar analysis was done to detect live FMDV on nasal swabs collected on 0-5 dpc. [Nasal swabs (Dacron polyester) were placed into chilled transport medium, mixed, removed, and samples frozen at −70° C.; thawed, centrifuged, and clarified samples (Spin-X centrifuge tube filters) were tested.]

Virus rRT-PCR Detection

Heparinized blood (plasma) samples collected from all cattle on 0-5 dpc were analyzed by rRT-PCR for the presence or absence of FMDV nucleic acid. The thermal profile for the rRT-PCR using the Applied Biosystems ABI 7500 platform was: hold at 60° C. for 10 minutes, run 45 cycles of denaturation at 95° C. for 30 seconds, linked to polymerization cycle of 60° C. for 1 minute. Individual rRT-PCR Ct values on 0-5 dpc were determined for each treatment group. In this assay, a $C_t$ value ≤40 was scored as positive (POS), and a $C_t$ value >40 was scored negative (NEG).

Viremia

For each treatment group, viremia following FMDV challenge was defined as positive or negative. Positive: CPE in cell culture and/or rRT-PCR $C_t$≤40 in any post-challenge sample collected and tested (days 1-5 post-challenge). Negative: No detectable CPE in cell culture and rRT-PCR $C_t$>40 in all samples collected and tested (days 1-5 post-challenge). For virus isolation from nasal swabs, only the presence or absence of CPE in culture was determined, and then analyzed as listed above. For each treatment group, protection against viremia was calculated according to the formula: (number of virus negative cattle)/(number of challenged cattle)×100%.

Summary

For each treatment group, protection against FMD generalized disease (pedal vesicular lesions) was determined. FMD clinical disease scores (pedal vesicular lesions) at four scoring time points were summarized for each animal and for each treatment as described. For each treatment group, percent protection against generalized FMD (pedal lesions) was calculated according to the formula: (number pedal lesion negative cattle)/(number of challenged cattle)×100%. The VP 4.2.1/VP 4.2.2 bivalent vaccine was considered efficacious if ≥75% of the vaccinated cattle fail to develop generalized disease while 100% of the placebo controls developed generalized disease following FMDV serotype A challenge. The results of all analyses are summarized in Table 2.

TABLE 2

Summary of clinical results

| Treatment Group | % Protection from Clinical Disease | % Protection Against Fever | % Protection Against Viremia (No. negative for live virus or rRT-PCR) | % Protection Against Nasal Shedding (No. negative for live virus) | % SVN Positive to FMDV Challenge Strain | |
|---|---|---|---|---|---|---|
| | | | | | 7 days post-vacc | Day of challenge |
| T01 PBS; FMDV A24 challenge | 0% (0/3) | 0% (0/3) | 0% (0/3) | 0% (0/3) | 0% (0/3) | 0% (0/3) |
| T02 VP4.2.1 and VP4.2.2; FMDV A24 challenge | 100% (3/3) | 33% (1/3) | 100% (3/3) | 0% (0/3) | 100% (3/3) | 100% (3/3) |
| T03 PBS; FMDV A Saudi Arabia 95 challenge | 0% (0/3) | 0% (0/3) | 0% (0/3) | 0% (0/3) | 0% (0/3) | 0% (0/3) |
| T04 VP4.2.1 and VP4.2.2; FMDV A Saudi Arabia 95 challenge | 100% (4/4) | 100% (4/4) | 100% (4/4) | 50% (2/4) | 100% (4/4) | 100% (4/4) |
| T05 PBS; FMDV A Iran-05 challenge | 0% (0/2) | 0% (0/2) | 0% (0/2) | 0% (0/2) | 0% (0/2) | 0% (0/2) |
| T06 VP4.2.1 and VP4.2.2; FMDV A Iran-05 challenge | 100% (4/4) | 75% (3/4) | 75% (3/4) | 100% (4/4) | 100% (4/4) | 100% (4/4) |

Two placebo animals died 5 days post-challenge (putative myocarditis). All other placebo animals developed disease, as summarized above. However, no disease was evident in any animals immunized with the mosaic vaccine (Fisher's Exact Test for Count Data p-value=$1.323 \times 10^{-5}$). These results demonstrate that the FMDV mosaic vaccine is highly efficacious against a broad range of wild-type serotype A FMDV strains.

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A synthetic polypeptide comprising an amino acid sequence at least 98% identical to SEQ ID NO: 2 or SEQ ID NO: 4.

2. The synthetic polypeptide of claim 1, comprising the amino acid sequence of SEQ ID NO: 2 or SEQ ID NO: 4.

3. A composition, comprising the synthetic polypeptide of claim 1 or claim 2, further comprising a pharmaceutically acceptable carrier.

4. The composition of claim 3, comprising a first synthetic polypeptide comprising the amino acid sequence of SEQ ID NO: 2, a second synthetic polypeptide comprising the amino acid sequence of SEQ ID NO: 4, and a pharmaceutically acceptable carrier.

5. The composition of claim 3, further comprising an adjuvant.

6. A recombinant foot-and-mouth disease virus (FMDV) comprising a synthetic polypeptide having an amino acid sequence at least 98% identical to SEQ ID NO: 2 or SEQ ID NO: 4.

7. The recombinant FMDV of claim 6, comprising a synthetic polypeptide comprising the amino acid sequence of SEQ ID NO: 2 or SEQ ID NO: 4.

8. A composition comprising the recombinant foot-and-mouth disease virus (FMDV) of claim 6, and a pharmaceutically acceptable carrier.

9. An isolated nucleic acid molecule encoding the synthetic polypeptide of claim 1.

10. The isolated nucleic acid molecule of claim 9, comprising the nucleotide sequence of SEQ ID NO: 1 or SEQ ID NO: 3.

11. A vector comprising the isolated nucleic acid molecule of claim 9.

12. The vector of claim 11, further comprising coding sequences for FMDV L, VP4, P2 and P3 proteins, whereupon transfection of the vector into a permissive host cell, infectious FMDV is produced.

13. A method of eliciting an immune response against serotype A foot-and-mouth disease virus (FMDV) in a subject, comprising administering to the subject a composition comprising a synthetic polypeptide at least 98% identical to SEQ ID NO: 2 or SEQ ID NO: 4, thereby eliciting an immune response to serotype A FMDV.

14. The method of claim 13, wherein the synthetic polypeptide comprises SEQ ID NO: 2 or SEQ ID NO: 4.

15. The method of claim 13, wherein the composition comprising the synthetic polypeptide further comprises a pharmaceutically acceptable carrier.

16. The method of claim 13, wherein the composition comprising the synthetic polypeptide further comprises an adjuvant.

17. The method of claim 13, comprising administering to the subject a first composition comprising a synthetic polypeptide at least 98% identical to the amino acid sequence of SEQ ID NO: 2 and a second composition comprising a second synthetic polypeptide at least 98% identical to the amino acid sequence of SEQ ID NO: 4.

18. The method of claim 17, wherein the first and second compositions are administered to the subject at different anatomical sites.

* * * * *